United States Patent [19]

Goldstein et al.

[11] Patent Number: 5,039,608

[45] Date of Patent: Aug. 13, 1991

[54] PROCESS FOR PREPARING ANTIGEN FRACTIONS DESIGNED FOR THE DETECTION OF ANTIBODIES INDICATIVE OF A CARDIOVASCULAR RISK CONDITION AND THEIR USE IN THE DIAGNOSIS OF A CARDIOVASCULAR RISK CONDITION

[75] Inventors: Israël Goldstein, Paris; Francois N. Marié, Orgeval, both of France

[73] Assignee: Diatech SA, Nanterre, France

[21] Appl. No.: 233,709

[22] Filed: Aug. 18, 1988

[30] Foreign Application Priority Data

Aug. 26, 1987 [FR] France .................. 87 11946

[51] Int. Cl.$^5$ .................. C12Q 1/00; G01N 33/535
[52] U.S. Cl. .................. 435/7.92; 435/7.1;
435/7.9; 435/28; 436/543; 436/63; 436/811;
530/356; 530/403; 530/827
[58] Field of Search .................. 435/7, 28, 177, 7.1,
435/7.9, 7.92; 436/527, 529, 530, 531, 543, 63,
811; 530/356, 403, 827

[56] References Cited

U.S. PATENT DOCUMENTS 4,343,734 8/1982 Lian et al. .
4,492,753 1/1985 Shell et al. .
4,628,027 12/1986 Gay .................. 436/811 X

OTHER PUBLICATIONS

Jokinen et al., Experimental and Molecular Pathology, vol. 42 (1985), pp. 4–6.
Chemical Abstracts, vol. 75, No. 17, Oct., 1971, p. 220, No. 107642m.
Goldstein et al., *Path. Biol.*, 34, 841 (1986).
Marie et al., Abstract 1–13, *Arch. Des. Mal. du Coeur et des Varsseaux*, 81, 24 (1988).
Furuto et al., *Methods in Enzymology*, 144, 41 (1987).
Robert et al., *Atherosclerosis*, 13, 427 (1971).
Goldstein et al., "Current Research Group A Streptococcus".
Caravano ed., p. 165, Excerpta Medica Foundation, Amsterdam, 1966.
Goldstein et al., *Nature*, 213, 44 (1967).
Goldstein et al., *Nature*, 219, 866 (1968).
Goldstein, Resume of Doctoral Thesis, 1.
Minick et al., *Amer. J. Path.*, 73, 265 (1973).

*Primary Examiner*—Sam Rosen
*Attorney, Agent, or Firm*—Armstrong, Nikaido, Marmelstein, Kubovcik & Murray

[57] ABSTRACT

The invention relates to a process for preparing antigen fractions designed for the detection of antibodies, the presence of which, in a certain quantity, in the human blood serum correlates with a cardiovascular risk condition. An arterial tissue is ground, freed of lipids and is subjected to the action of at least one agent selected from the group formed by an aqueous solution of an alkali metal salt or of an alkaline-earth metal salt at ambient temperature, of a hot acid of urea, of guanidine and proteolytic enzymes. The invention also relates to antigen fractions thus obtained and their utilization in the diagnosis of a cardio-vascular risk condition by counter-current electrophoresis or by an ELIFA test or an ELISA test.

16 Claims, 1 Drawing Sheet

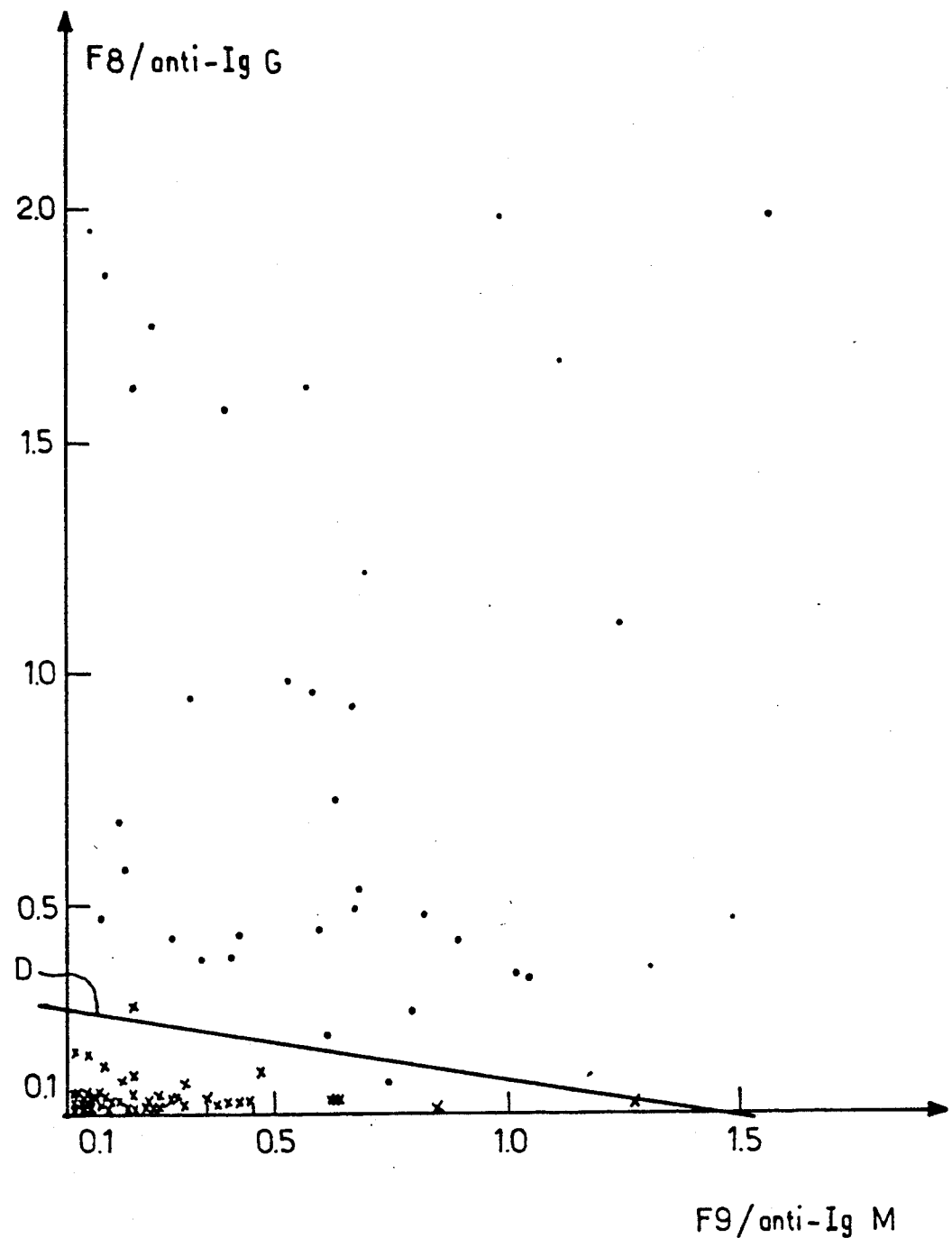

PROCESS FOR PREPARING ANTIGEN FRACTIONS DESIGNED FOR THE DETECTION OF ANTIBODIES INDICATIVE OF A CARDIOVASCULAR RISK CONDITION AND THEIR USE IN THE DIAGNOSIS OF A CARDIOVASCULAR RISK CONDITION

The present invention relates to a process for preparing antigen fractions designed for the detection of autoantibodies the presence of which in a certain quantity in the human blood serum correlates with risk of a cardiovascular accident in the individual. The invention also relates to the antigen fractions thus obtained and to their use in the diagnosis of a cardiovascular risk condition, be it by electrosyneresis or by an ELIFA-type test or by an ELISA-type test.

It is known that cardio-vascular diseases and, in particular, atherosclerosis are one of the major causes of death in the developed countries. This affliction is ubiquitous and is promoted by a large variety of factors, among which may be mentioned dynamic factors such as arterial hypertension, metabolic factors such as diabetes or the increase of lipid concentration in the blood, toxic factors such as excessive smoking or alcohol consumption. Atherosclerosis manifests itself by a stiffening of the arteries, owing to the formation of obstructing plaques in the interior of the arterial tissue itself. This plaque formation leads to a reduction of the arterial cross-section and to a diminution of the elasticity and contractility of the elastic muscular fibres in the zone where the plaque is formed. This phenomena has already been widely studied (see in particular GOLDSTEIN, FONTALIRAN, MARIE, GAY, Pathologie Biologie, 1986, 34, No. 7, 841-846); thus, it is known that these plaques with calcic deposits are in general formed in the junction zone between the inner layer (or intima) and the middle layer (or media) of the arterial tissue. Since the intima and the media are practically not irrigated, they are fed and oxygenated by the bloodstream circulating in the artery or by the bloodstream which passes through the blood vessels of the external layer (or adventitia) of arterial tissue. Once formed, the deposit is thus located in a zone from which it practically cannot be extracted, with the result, that the disease practically cannot regress.

Moreover, it has been shown in the prior art referred to, that the lesions caused by an atherosclerosis lead to the formation of an antibody. It is known that the human body does not produce antibodies against its own tissues as long as these are normal; however, if the tissue is injured, it becomes biochemically different and by itself constitutes a neo-antigen. The body therefore produces antibodies against these neo-antigens and these antibodies attach themselves to the atherosclerotic plaques. There are thus formed neoantigen-/autoantibody complexes and these complexes in turn increase the size of the atherosclerotic deposit, so that the disease, once established in the individual, is self-maintained by the immunological phenomena described above. This auto-immune disease therefore has a self-aggravating tendency from its very onset, and this is the reason why it is extremely desirable to have on hand tests enabling the detection in an individual the appearance of the immunological component of the disease and thus the level of the risk of a corresponding cardiovascular accident.

It is known that the immunoglobulins are the raw materials for the production of specialised antibodies. In the previously cited prior publication, it has been shown that, on the sites of atherosclerotic plaque lesions, immunoglobulins and the complement ($C_3$) could be found. According to the present invention, it was thus conceived to locate in the blood serum of a subject to be studied those immunoglobulins which are likely to have been produced in the subject's body for fixation on the atherosclerotic zones of the arterial system of the subject. With this end in view, according to the invention, there are prepared antigen fractions which are caused to react in vitro with the serum of the subject being studied, the result of the reaction being revealed in an appropriate manner by detecting and eventually measuring the quantity of the antigen-antibody complex formed.

The present invention accordingly has for an object a process for preparing antigen fraction or fractions designed for the detection of autoantibodies the presence of which, in a certain quantity, in the blood serum of an individual correlates with the level of cardiovascular risk condition of the said subject, characterised in that, in a first phase, there is produced a ground homogenate of human arterial tissue constituting the raw material for the desired fractions; that in a second phase said homogenate is freed of lipids by treatment with solvent(s) at ambient temperature; that in a third phase the solid residue of the second phase is treated by subjecting its constituents, in order to obtain a plurality of proteinic fractions, to the action of at least one agent taken from the group formed by an aqueous solution of a salt of an alkali metal or an alkaline-earth metal at ambient temperature, a hot acid, urea, guanidine or proteolytic enzymes.

According to a first variant, during the above-mentioned third phase, the solid residue of the second phase is subjected to a treatment with aqueous solution or solutions of an alkali or an alkaline-earth metal, the residue of this operation is then subjected to treatment with an acid at elevated temperature, whereafter all or part of the new residue thus obtained is subjected to the action of one or the other treating agents listed. Following the treatment with acid at elevated temperature, the non-solubilised residue can be advantageously fractioned in four parts, the first part being subjected, at ambient temperature, to the action of an aqueous urea solution, the second part being subjected at ambient temperature to the action of an aqueous solution of guanidine, the third part being subjected to a treatment with elastase between 30° and 45° C. and the fourth part is subjected to a treatment with pronase between 30° and 45° C. The enzymatic treatments of the third and fourth part of the residue are preferably carried out at a pH between 8.3 and 9.2 and said treatments are maintained for a period of 8 to 16 hours, said treatments being thereafter stopped by heating to 60°-70° C. for at least 60 minutes. Also preferably, the first part of the residue is subjected to the action of an aqueous solution of urea at a pH between 5.5 and 6.5, at a concentration of between 7 and 9 moles/liter, while stirring, for 20 to 30 hours, and the second part of the residue is subjected to the action of an aqueous guanidine solution at a pH comprised between 5.5 and 6.5, at a concentration comprised between 3 and 5 moles/liter, while stirring, for 20 to 30 hours.

According to a second variant, in the third phase of the process of preparation according to the invention, the solid residue of the second phase is subjected to the treatment with aqueous solution(s) of an alkali-metal or alkaline-earth metal salt(s), the liquid fractions obtained are recovered to reform the collagen fibres according to the process described in French Patent Application 87-09297 U.S. application Ser. No. 214,346 filed July 1, 1988 and incorporated herein by reference and said reconstituted fibres are treated with one of the treating agents provided for the said third phase. Advantageously, the reconstituted fibres are divided in five parts, the last four parts being each submitted to one of the treatments selected from the group of treatments constituted by the treatments with urea, guanidine and with the previously named enzymes, the first part being subjected to a hot acid treatment.

In one or the other of the above-mentioned variants, the hot acid treatment is advantageously carried out with an aqueous solution of trichloroacetic acid at a concentration comprised between 0.1 and 0.5 mole/liter, at a temperature comprised between 85° and 105° C., during a time period comprised between 15 and 45 minutes.

The invention also has for object, by way of a new industrial product, the antigen fractions obtained in the form of aqueous solutions in the above-defined process.

The application of the above-defined antigen fractions for the detection of antibodies in the serum of the subject to be examined can be carried out by one or the other of three techniques the principle of which is well known to those skilled in the art: firstly, electrosyneresis (see in particular COONROD, J. D., and RYTEL, M. W., J. Lab. Clin. Med., 81, 770 (1973)), secondly the ELIFA method (see in particular Journal of Immunological Methods, 77 (1985), 15–23), and finally the ELISA method (see in particular ENGVALL and RUOSHLATI, 1977, Int. J. Cancer, 20, 1), the latter enabling a quantitative evaluation to be made while the first two allow a qualitative evaluation only of the cardiovascular risk condition.

Accordingly, the present invention also has for object the utilization of at least one antigen fraction such as defined above for the diagnosis of a cardiovascular risk condition, characterised in that there is carried out an electrosyneresis by applying in an appropriate support, firstly a liquid containing at least one of the aforesaid antigen fractions and, secondly, the blood serum of the aforesaid subject. In a first variant, the electrosyneresis support is an agarose gel; in a second variant, said support is a cellulose acetate strip. Advantageously, the potential difference between the reservoir zones respectively occupied by the antigen-containing liquid and the serum is maintained between 100 and 200 Volts for approximately 60 to 90 minutes. With this technique, the immunoglobulins of the serum being examined migrate towards the negative pole, whilst the majority of the other constituents of the serum as well as the antigens of the antigen-containing liquid migrate towards the positive pole. The immunoglobulins thereby meet the antigens to which they are specific, and bind to these antigens to form complexes. These antigen/antibody complexes are formed in a plane or cylindrical combination zone disposed between the reservoir zones occupied by the antigen-containing liquid and the serum.

To reveal the presence of these complexes and to obtain the desired qualitative indication, it is possible to proceed by colouring the complexes. In a first variant, the support is immersed in a colorant having an affinity for proteins, then into a bleaching agent the action of which leaves present only the coloured trace of the antigen-antibody complexes. Advantageously, Coomasie Blue is utilized as colorant. In a second variant, the support is treated with animal immunoglobulins having anti-human immunoglobulin action (hereafter referred to as "anti-Ig"), said anti-Ig's being marked with peroxydase in a known manner (see in particular AVRAEMAS, S., Int. Rev. Cytol., 1970, 27, 349–387 and Imunochemistry, 1976, 6, 43–49); the revealing of the anti-Ig's fixed by the serum antibodies, which have complexed with the antigens of the antigen-containing liquid during the electrosyneresis is effected by means of a mixture formed of a coloration-precursor substrate and hydrogen peroxide; as a coloration precursor there may be employed diamino-benzidine.

According to the third technique, there can be employed in an ELISA test at least one antigen fraction according to the invention, thus making it possible to quantify the diagnosis of a cardiovascular risk condition in a living subject. According to this technique, the antigen-containing liquid is placed in a vessel having a pretreated surface and containing a buffered medium with a pH between 8.5 and 9.5. The contents are allowed to evaporate to dryness and the vessel is washed. The vessel is then saturated with an aqueous solution of serum albumin of animal origin, buffered to a pH between 7 and 7.6 for 15 to 45 minutes at ambient temperature; the serum to be examined is diluted in a buffer having a pH between 7 and 7.6 in a ratio comprised between 1/50 and 1/2000 and is then poured into the vessel, adding thereto serum albumin of animal origin. After a contact period of 30 to 60 minutes, the vessel is washed with physiological water and the anti-Ig's of animal origin are added, marked in a known manner with peroxidase. Following a contact period of 30 to 60 minutes, the vessel is washed and the complexes (antigen-antibody-anti-Ig) formed are revealed by an aqueous solution of coloration precursor (substrate) in the presence of hydrogen peroxide, the revelation being arrested after a chronometer-measured period of 4–5 seconds. The intensity of the coloration obtained due to the presence of these complexes containing the marked anti-Ig's is read and the numerical evaluation of the cardiovascular risk condition is deduced therefrom.

Advantageously, the aqueous solution of the colorant precursor employed for this ELISA test is a solution of orthophenylene-diamine, buffered to a pH between 4.8 and 5.1 and the stopping of the revelation is effected by the addition of an aqueous solution of sulphuric acid and sodium pyrosulphite.

In order to make better understood the object of the invention, a description will be given in the following, by way of purely illustrative and non-limiting examples, of two modes of execution of the process for preparing the antigen fractions in question, and three modes of application of these said antigen fractions for detecting cardiovascular risk conditions in a subject.

The antigen fractions are prepared from a human arterial tissue. For example, a human aorta is dissected so as to separate the adventitia from the intima and the media, keeping only the latter two. This raw material is cut into strips of about 0.5 cm wide. This is followed by a washing with water by immersing this material into one hundred times its volume of water for 24 hours while stirring lightly. After this, the raw material is ground in a grinder of the "Magimix 3500" type for 15 minutes.

The material thus obtained is freed of lipids by placing it first into ten times its volume of ethyl ether for 24 hours while stirring lightly, the subjecting the insoluble residue to ten times its volume of chloroform, for 24 hours, while stirring lightly. The result of the first extraction is a fraction $F_1$; the second extraction yields a fraction $F_2$.

The solid residue is thereafter subjected, following grinding, to the action of an aqueous solution containing a "PBS" buffer constituted by monosodium and disodium phosphate in a concentration of 0.01 mole/liter in proportions providing for a pH of 7.3, admixed with 0.9% NaCl, and further containing 1 mole/liter of sodium chloride. This treatment is sustained while stirring at 4° C. for 24 hours. The solid residue is then separated from the liquid phase and is subjected, after grinding, to the action of an aqueous solution buffered with the above-mentioned PBS buffer, said solution containing moreover 2 moles/liter of sodium chloride, the treatment being carried out while stirring at 4° C. for 24 hours. The liquid phase is separated and mixed with the previously separated liquid phase to form a fraction $F_3$. The solid residue is placed after grinding into a buffered aqueous solution (PBS-buffer) of calcium chloride of 1 mole/liter, this extraction being carried at 4° C. while stirring vigorously for 24 hours. At the end of the extraction, the liquid phase and the solid residue are separated. In this manner, there are carried out in succession five identical extractions with an aqueous molar solution of calcium chloride. The five liquid extracts obtained are mixed together and the solid residue is taken up in a sixth extraction carried out with a buffered aqueous solution (PBS-buffer) of calcium chloride of 2 moles/liter, for 24 hours at 4° C. while stirring vigorously. There is obtained in this manner a new liquid extract which is mixed to the five preceding ones to obtain a fraction $F_4$. The fractions $F_3$ and $F_4$ are mixed together.

The fractions $F_1$ and $F_2$ contain the lipoproteins of the treated arterial tissue. The fractions $F_3$ and $F_4$ contain the hydrosoluble proteins and glycoproteins and, by referring to French Patent Application 87-09297, it is seen that the fractions $F_3$ and $F_4$ can be employed for the manufacture of reconstituted collagen fibres. Leading from this observation, the process of preparation may proceed according to two distinct variants.

In the first variant, the non-solubilised residue obtained after the last extraction with calcium chloride is taken up and treated with 10 volumes of trichloroacetic acid of 0.25N concentration for 1 volume of residue. This treatment is carried out at 96° C. for 30 minutes while stirring. There is obtained in this manner a liquid phase $F_5$ which contains the denaturated acid-soluble collagen; the residue not solubilised is isolated and divided into four equal parts.

The first part is then treated with an 8 moles/liter aqueous urea solution; the solution is at pH 6. The treatment is continued while stirring for 24 hours and there is obtained in this manner a liquid phase $F_6$.

The second part of the solid residue is treated with a 4 moles/liter aqueous guanidine solution; the pH of the solution is 6. The treatment is continued for 24 hours while stirring. There is obtained in this manner a liquid phase $F_7$.

The third part of the residue is treated with pig pancreatic elastase, at a rate of 1 mg for 100 mg residue. The treatment is carried out at pH 8.8 in a TRIS-HCl buffer (TRIS=trihydroxymethylaminomethane), at 37° C. for 12 hours. The reaction is stopped by heating the medium to 65° C. for 1 hour. There is obtained in this manner a liquid phase $F_8$.

The fourth part is treated with pronase (enzyme of the streptomyces griseum) at a rate of 1 mg of enzyme for 100 mg of residue. The treatment is carried out at pH 8.8 in a 0.1 mole TRIS-HCl buffer in the course of 12 hours at 37° C. The reaction is stopped by heating to 65° C. for one hour. There is obtained in this manner a liquid phase $F_9$.

In the second variant of this manufacturing process, there is taken a portion of the fractions $F_3/F_4$ which contain all the soluble proteins of the initial arterial tissue and reconstitute from this liquid phase the collagen fibres according to the process described in French Patent Application 87-09297, the contents of which Application are incorporated into the present Application by way of reference. The reconstituted fibres thus obtained are then collected and divided in five equal parts.

The first part of the fibres is subjected to the action of trichloroacetic acid at 96°, as previously indicated for the first variant; there is obtained in this manner a liquid fraction $F_5'$. The second part of the fibres is treated with an aqueous urea solution as indicated for the first variant; there is obtained in this manner a liquid fraction $F_6'$. The third part of the fibres is treated with an aqueous guanidine solution as in the first variant; there is obtained in this manner a liquid fraction $F_7'$. The fourth part of the fibres is treated with elastase, as indicated in the first variant; there is obtained in this manner a liquid fraction $F_8'$. The fifth part is treated with pronase, as in the first variant; there is obtained in this manner a liquid fraction $F_9'$.

When, in this manner, the liquid fractions $F_1$ to $F_9$ or $F_1$ to $F_4$ and $F_5'$ to $F_9'$ have been obtained, there are available antigen fractions capable of detecting the autoantibodies produced by an individual affected by atherosclerosis. The reactions of the different antigens corresponding to these different fractions are different for the diagnosis and the diagnostic method will accordingly consist in applying a set of tests utilizing the different antigen-containing fractions prepared in the above manner. The search for these antibodies reacting to fractions $F_1$ and $F_2$ corresponds to the search for the complexes (antigen-antibody) with lipid deposits. The search for the antibodies reacting to the fractions $F_3$ and $F_4$ corresponds to the search for antigen-antibody complexes arising with soluble proteins: soluble glycoproteins, proteoglycans, procollagen, proelastin and, above all, fibronectin. The search for antibodies reacting to the fraction $F_5$ corresponds to the formation of antigen-antibody complexes due to structural (insoluble) collagen. The search for antibodies specific to fractions $F_6$ and $F_7$ corresponds to the formation of antigen-antibody complexes with structural glycoproteins. The search for antibodies to fractions $F_8$ and $F_9$ corresponds to the formation of antigen-antibody complexes with collagen-base glycopeptides, elastine and sugars (aminosugars, neuraminic acid, and mannose, galactose, glucose.

There are three different methods for the utilization of these antigen-containing fractions.

In the first method, there is carried out an electrosyneresis, that is to say, a counter-current electrophoresis according to the technique described by CONROOD and RYTEL (document previously cited). There is prepared a strip of agarose gel, in which two cavities are formed, into which cavities are placed, respectively, one of the antigen-containing fractions previously obtained and the serum of the individual to be examined. The strip of agarose gel, which has a length of 60 mm, is subjected to a potential difference of 120 Volts, the current being approximately 2 milliamps. The pH of the agarose gel is maintained at 8.8 by means of a 0.1 molar TRIS-glycine buffer. The positive pole is placed on the side of the serum to be examined; the immunoglobulins of the said serum migrate towards the negative pole, while the antigens of the antigen-containing liquid migrate towards the positive pole. Thus, the application of a potential difference brings about the encounter of corresponding specific antigens and immunoglobulins on a plane or cylindrical surface positioned between the two reservoir zones. In this combination zone there is formed an antigen-antibody complex.

After 70 minutes of electrosyneresis, the gel strip is immersed for 7 minutes in a 1.5% by weight solution of Coomasie Blue in ethanol/acetic acid/water in proportions of 4/1/5 by volume; the dyestuff preferentially colours the proteins, that is to say, the antigen-antibody complexes formed. After washing the gel strip, the latter is immersed into a bleaching solution composed of acetic acid/ethanol/water in a weight ratio of 1/4/5 during 7 minutes. In this manner, a bleaching of the gel is obtained, there remaining coloured only the complexes formed in the combination zone. There is achieved in this manner a qualitative determination, in the serum to be examined, of the presence of antibodies characterising a cardiovascular risk condition.

According to a second technique, the above-mentioned electrosyneresis is carried out on a cellulose acetate strip instead of using an agarose gel strip. The cellulose acetate strip can likewise be revealed with Coomasie Blue, but it is also possible to apply the technique called ELIFA described by PINON, THOANNES and GRUSON, Journal of Immunological Methods, 77 (1985), 15–23. In this case, on the support strip there are caused to act immunoglobulins of animal origin with anti-human immunoglobulin specificity. These anti-immunoglobulins (anti-Ig) can be specific to G, M, A and E-type human immunoglobulins. These anti-Ig's are marked with peroxidase according to the technique of AVRAEMAS (documents previously cited). In the combination zone of the cellulose acetate strip there are formed antigen-antibody complexes and the anti-Ig utilized attaches itself to the corresponding antibody of the complex. There is obtained in this manner a complex of antigen/antibody/anti-Ig, the presence of which can be revealed by reaction with orthophenylene-diamine in the presence of hydrogen peroxide. The red colouring reveals the existence in the serum examined of antibodies of the type corresponding to the anti-Ig employed.

According to a third technique, there is carried out a test enabling a quantitative evaluation to be made of the antibodies in the serum examined; this test corresponds to the ELISA technique. There is employed a surface-treated polyvinyl plate, supplied by the firm named "NUNC", said plate comprising a plurality of cups. Into a cup is placed 150 $\mu$l of 0.05 mole sodium carbonate buffer at pH 9 and 0.1–1 $\mu$g of any one of the antigen-containing fractions prepared as indicated above. The plate is left at 37° C. for 12 hours and thereafter at ambient temperature for 72 hours to achieve complete dryness. The cup thus prepared is then washed with physiological water containing 0.2% of a detergent marketed under the trade name of "TWEEN 20" (a mixture of sorbitol lauryl ester and sorbitol anhydride, principally ethylene-oxidic sorbitan monolaureate with 20 mols of ethylene oxide). This washing operation is carried out by three successive washings of 5 minutes each. There is the added to the cup 200 $\mu$l of bovine serum-albumin at a concentration of 1 vol.-% in a "PBS" buffer, the pH being thus maintained at 7.3. The serum albumine is left in contact with the cup for 30 minutes at ambient temperature, after which the cup is emptied: this saturation with serum albumine effects the occupation within the cup of the sites not occupied by antigen.

The human serum to be examined is prepared in a dilution to 1% by weight in a "PBS" buffer, said buffer being admixed with 1 volume-% of bovine serum albumin and 0.2% by volume of a detergent marketed under the trade name of "TWEEN 20". There are placed in the cup in question 100 $\mu$l of the serum diluted as indicated above and left in the cup for 30 minutes at ambient temperature. The antibodies of the serum can only attach to the sites occupied by the antigens, the other sites being blocked by the serum albumin.

After emptying the cup, the latter is washed five times in succession with physiological water admixed with 0.2% by volume of the "TWEEN 20" detergent. There are then added to the cup 100 $\mu$l of rabbit anti-human immunoglobulins (called "anti-Ig"). These anti-Ig's are marked with peroxidase in a known manner; they are employed in a concentration of 1/5,000 in the same "PBS" buffer as used for diluting the human serum. The anti-Ig's are left in the cup for 30 minutes at ambient temperature. The cup is then emptied and is subjected to five successive washing operations like before the introduction of the anti-Ig's.

During the preceding operations, there was fixed to the walls of the cup the antigen corresponding to the antigen-containing fraction, followed by the introduction in the serum to be examined of the antibody specific to said antigen. Thus, the antigen-antibody complex has been formed, following which, the anti-Ig's corresponding to the antibodies of the complex were introduced. In this manner a complex (antigen/antibody/anti-IG) has been formed and this complex is marked with peroxidase, because the anti-Ig fixed was peroxidase-marked. There thus remains the task of revealing this peroxidase-marked complex.

To effect this, there is prepared a 4 mg/ml solution of orthophenylene-diamine in a 0.1 mole/liter sodium citrate buffer (pH=5) to which is added hydrogen peroxide of 110 volume strength at a rate of 2 $\mu$l per ml of buffer. 100 $\mu$l of this solution are placed in the cup which served as reaction vessel. A brown colouring appears. The reaction is stopped after 6 minutes by adding to the cup 100 $\mu$l of 2N sulphuric acid to increase the pH, admixed with 2% by weight of sodium pyrosulphite to destroy all traces of oxidising agent.

The contents of the cup thus coloured are then read in an optical reader with two beams operating at 490 nanometers. The reader is of the type "M 700", marketed by the "DYNATECH" Company. The values of colorimetric intensity are noted after subtraction of the value corresponding to the background colouring. With the above-mentioned reading instrument, the values of O.D. between 0.2 and 2 are considered as pathological in a proportional measure.

In this technique, the polyvinyl plates generally have a sufficient number of cups so as to enable the tests to be carried out with the entire range of the antigen-containing fractions prepared in the above-described manner and with the anti-Ig's specific to the G, A, M and E type human immunoglobulins.

The tests carried out regarding the different antigen-containing fractions $F_1$ to $F_9$ or $F_1$ to $F_4$ and $F_5'$ to $F_9'$ have shown, by using for the ELISA tests the type G, M, A and E anti-Ig's, that there were obtained, depending on the coupling (antigen-containing fraction/anti-Ig of a given type), different diagnostic features. By way of example, in the following are given the results obtained when using the antigen-containing fractions $F_8$ and $F_9$ and the type G or M anti-Ig's. In the following table, the figures represent optical densities read on the previously mentioned optical reader.

The group of patients included 29 patients with an average age of 60 years. The young reference group included 44 subjects, with an average age of 20 years. The aged reference group included 30 subjects with an average age of 64 years.

TABLE I

|  |  | young reference group | aged reference group | patients |
|---|---|---|---|---|
| Number of subjects |  | 44 | 30 | 29 |
| Antigen fraction $F_8$ and type G anti-Ig | mean | 0.06 ± 0.09 | 0.08 ± 0.06 | 0.71 ± 0.54 |
|  | median | 0.04 | 0.06 | 0.46 |
| Antigen fraction $F_9$ and type G anti-Ig | mean | 0.37 ± 0.43 | 0.36 ± 0.26 | 0.84 ± 0.39 |
|  | median | 0.02 | 0.03 | 0.83 |
| Antigen fraction $F_8$ and type M anti-Ig | mean | 0.08 ± 0.09 | 0.14 ± 0.14 | 0.49 ± 0.44 |
|  | median | 0.06 | 0.095 | 0.33 |
| Antigen fraction $F_9$ and type M anti-Ig | mean | 0.18 ± 0.25 | 0.16 ± 0.12 | 0.7 ± 0.39 |
|  | median | 0.08 | 0.12 | 0.65 |

It is seen that there is little difference between the young and aged reference groups but, on the other hand, there is a considerable difference between the reference groups and the patient group.

The single figure shows a graph in which each subject tested according to the invention corresponds to a point on the graph. The abscissa of this point is the value of the optical density read on the above-mentioned reader for a test corresponding to the fraction $F_9$ with a M-type anti-Ig, while the ordinate of this point corresponds to the optical density read on the above-mentioned instrument for an antigen-containing fraction $F_8$ with the G-type anti-Ig's. It is seen in particular that all patients have coordinate points situated above the straight line D, whereas all the healthy subjects have coordinate points situated below the said line D (the points corresponding to reference individuals are in the form of a cross, whilst those corresponding to the members of the patient group are indicated by a round point).

The same experimental results have been treated statistically in a different manner, all reference individuals being considered as a single group relative to the patient group. By carrying out the correlations, the following tabulation is obtained:

TABLE II

|  | Anti-Ig G/$F_8$ | Anti-Ig M/$F_8$ | Anti-Ig G/$F_9$ | Anti-Ig M/$F_9$ |
|---|---|---|---|---|
| Anti-Ig G/$F_8$ | 1 |  |  |  |
| Anti-Ig M/$F_8$ | 0.37 | 1 |  |  |
| Anti-Ig G/$F_9$ | 0.64 | 0.4 | 1 |  |

TABLE II-continued

|  | Anti-Ig G/$F_8$ | Anti-Ig M/$F_8$ | Anti-Ig G/$F_9$ | Anti-Ig M/$F_9$ |
|---|---|---|---|---|
| Anti-Ig M/$F_9$ | 0.48 | 0.82 | 0.4 | 1 |

It is seen that the fractions $F_8$ and $F_9$ associated with the type G or type M anti-Ig are of particular interest in the overall evaluation of cardiovascular risk condition.

It has been observed, moreover, that the results of the measurements carried out with the test according to the invention with the antigen-containing fractions $F_5$, $F_7$ and $F_8$ on one hand and the type M anti-Ig on the other, are considerably higher-valued on the first day of an infarction and persist at a high level for at least one month. The same observation has been made with the antigen-containing fraction $F_8$ associated with the type A anti-Ig. It may be thought that the antigens corresponding to Fractions $F_5$, $F_7$ and $F_8$ stimulate primarily the type M immunoglobulins and pre-exist prior to the myocardial infarction.

It has been found in addition that the increase of the type M antibodies (Ig M) against the antigens of fractions $F_5$, $F_7$ and $F_8$ on the fourteenth and 28th day after the myocardial infarction is a component of the total Ig M-stimulation by the infarction.

| 14th day: total Ig M | $F_5$/Ig M | r = 0.609 |
|---|---|---|
|  | $F_7$/Ig M | r = 0.702 |
|  | $F_8$/Ig M | r = 0.680 |
| 28th day: total Ig M | $F_5$/Ig M | r = 0.739 |
|  | $F_7$/Ig M | r = 0.917 |
|  | $F_8$/Ig M | r = 0.711 |

On the twenty-eighth day after a myocardial infarction there exists a linear correlation between the titer of the "anti-smooth muscle" antibody and the Ig M antibodies against the antigen-containing fraction $F_5$ (r=0.722), the fraction $F_5$ (r=0.722), the fraction $F_7$ (r=0.916) and the antigen-containing fraction $F_8$ (r=0.669).

We claim:

1. A process for preparing antigen-containing fractions of human arterial tissue, said antigens being reactive with at least one circulating antibody characteristic of atherosclerotic cardiovascular disease, said process comprising:
   a) preparing a homogenate of human arterial atherosclerotic tissue;
   b) solvent-extracting said homogenate at room temperature to remove lipids;
   c) fractionating the product of step b) by treatment with at least one agent selected from the group consisting of:
      i) an ambient temperature aqueous solution of a salt of an alkali metal or an alkaline earth metal;
      ii) a hot aqueous solution of a strong carboxylic acid
      iii) a concentrated aqueous solution of urea
      iv) an aqueous solution of guanidine; and
      v) a suspension of a proteolytic enzyme and
   d) isolating the extracted antigen.

2. A process according to claim 1, wherein a residue of the treatment with a salt solution in step c)i) is further treated with at least one of the agents selected from the group consisting of:
   ii) a hot aqueous solution of a strong carboxylic acid iii) a concentrated aqueous solution of urea
iv) an aqueous solution of guanidine; and
v) a suspension of a proteolytic enzyme.

3. A process according to claim 2 wherein aliquots of said residue remaining from treatment with a salt solution and a hot carboxylic acid are treated, separately, with
   an ambient temperature concentrated aqueous solution of urea;
   an ambient temperature aqueous solution of guanidine;
   a suspension of elastase at a temperature between 30° and 45° C., and
   an aqueous suspension of pronase at a temperature of 30°–45° C.

4. A process according to claim 3, wherein said treatment with aqueous urea is conducted with stirring for 20 to 30 hours, said solution having a concentration of 7 to 9M and a pH between 5.5 and 6.5.

5. A process according to claim 3 wherein said treatment with aqueous guanidine is conducted with stirring for 20 to 30 hours, said solution having a concentration of 3 to 5M and a pH of 5.5 to 6.5.

6. A process according to claim 3, wherein the aqueous fraction obtained by treatment with an ambient temperature aqueous solution of a salt is converted to collagen fibers and said fibers are further treated with at least one agent selected from:
   ii) a hot aqueous solution of a strong carboxylic acid
   iii) a concentrated aqueous solution of urea
   iv) an aqueous solution of guanidine; and
   v) a suspension of a proteolytic enzyme.

7. A method for measuring the degree of development of atherosclerotic cardiovascular disease in a human comprising measuring the degree of antigen-antibody complex formation when blood serum from said human is brought into contact with an antigen obtained by the process of claims 2, or 5.

8. A method according to claim 7, wherein said method of measuring of the degree of Ag-Ab complex formation is by countercurrent electrophoresis, wherein said blood serum and an antigen-bearing liquid containing at least one of said antigens, are applied to a suitable support and caused to complex by migration in an electrical field.

9. A method according to claim 8 wherein said support is selected from the group consisting of agarose gels and a cellulose acetate strips, and potential difference of 100 to 200 V is applied between reservoir zones containing said respective Ag and Ab, for a period of 60 to 90 minutes.

10. A method according to claim 8 wherein after complex formation said support is immersed in a stain having a affinity for proteins and is developed by bleaching out stain not complexed with said Ag-Ab complex.

11. A method according to claim 8 wherein said Ag-Ab complex is identified by treating said support with anti-human animal immunoglobins labeled with peroxidase and developed using a peroxidase substrate which is a chromophore precursor.

12. A method according to claim 11, wherein said precursor is orth-phenylenediamine.

13. A process according to claim 3, wherein said the enzyme treatments are carried out at a pH between 8.3 and 9.2, and that said treatments are continued for a period of time between 8 and 16 hours, said treatments being then stopped by heating the medium to 60°–75° C. for at least 30 minutes.

14. A process according to any one of claims 2 and 6, wherein said hot acid treatment is carried out by means of an aqueous solution of trichloroacetic acid in a concentration comprised between 0.1 and 0.5 mole/liter, at a temperature comprised between 85° and 105° C. for a period comprised between 15 and 45 minutes.

15. A method according to claim 7, wherein:
   the antigen-bearing liquid is placed in a vessel having a previously treated surface containing a buffered medium with a pH comprised between 8.5 and 9.5, whereafter the medium is left to evaporate and the vessel is washed;
   the vessel is saturated with an aqueous solution of animal serum albumin buffered to a pH comprised between 7 and 7.6, for 15 to 45 minutes at ambient temperature;
   the serum to be examined is diluted in a buffer with a pH between 7 and 7.6 in a proportion between 1/50 and 1/2000, whereafter it is poured into the vessel, adding thereto animal serum albumin to saturate unoccupied binding sites;
   after a contact time between 30 and 60 minutes, the vessel is washed with physiological water and the labeled animal "anti-Ig's" are added, said label being effected with peroxidase;
   after a contact period of between 30 and 60 minutes, the vessel is washed and the antigen/antibody/anti-Ig complexes formed are revealed by means of a colouring precursor substrate in the presence of hydrogen peroxide, the revelation being stopped after a predetermined time;
   the intensity of colouring due to the presence of the complexes containing the labeled anti-Ig's is read and from this reading the evaluation of the cardiovascular risk condition is made.

16. A method according to claim 15, characterised in that there is employed by way of colouring precursor orthophenylene-diamine, buffered to a pH between 4.8 and 5.1, the stopping of the colorimetric revelation being obtained by the addition of an aqueous solution of an acid and of a reducing agent.

* * * * *